US00PP07949P

United States Patent [19]

Warriner

[11] Patent Number: Plant 7,949

[45] Date of Patent: Aug. 25, 1992

[54] ROSE PLANT JACYEF

[75] Inventor: William A. Warriner, Tustin, Calif.

[73] Assignee: Bear Creek Gardens, Inc., Medford, Oreg.

[21] Appl. No.: 625,930

[22] Filed: Dec. 10, 1990

[51] Int. Cl.[5] ..... A01H 5/00

[52] U.S. Cl. ..... Plt./15

[58] Field of Search ..... Plt./15, 24

*Primary Examiner*—Howard J. Locker

*Attorney, Agent, or Firm*—Klarquist, Sparkman, Campbell, Leigh and Whinston

[57] ABSTRACT

A Grandiflora class rose plant having vigorous upright habit of growth, non-fading yellow flowers, resistance to rust, tolerance to blackspot, and high production of flowers suitable for cutting from the garden.

1 Drawing Sheet

The present invention relates to a new and distinct variety of rose plant of the Grandiflora class which was originated by me by crossing the variety Sunbright, U.S. Plant Pat. No. 4,438, with the variety Sunflare, U.S. Plant Pat. No. 5,001.

The primary objective of this breeding was to produce a new rose variety having the excellent color stability and flower form of Sunbright combined with the very heavy flower production and disease resistance of Sunflare. The objective was substantially achieved along with other desirable improvements as evidenced by the following unique combination of characteristics which are outstanding in the new variety and which distinguish it from its parents, as well as from all other varieties of which I am aware:

1. Vigorous, upright habit of growth.
2. Non-fading yellow flower.
3. Resistance to rust and tolerance to blackspot.
4. High production of flowers suitable for cutting from the garden.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent.*—Sunbright, U.S. Plant Pat. No. 4,438.

*Pollen parent.*—Sunflare, U.S. Plant Pat. No. 5,001.

Classification:

*Botanical.*—Rosa hybrida.

*Commercial.*—Grandiflora.

FLOWER

Observations made from specimens grown in a garden in Somis, Calif., in September, 1990.

Blooming habit: Continuous.

Bud:

*Size.*—1¼ inches when the petals start to unfurl.

*Form.*—Short, pointed ovoid.

*Color.*—When sepals first divide, bud color is Yellow Group 13B. When half blown, the upper sides of the petals are Yellow Group 12B; and the lower sides of the petals are Yellow Group 12B.

*Sepals.*—Color: Green Group 138B. Surface texture: Covered with fine hairs. Three are three normally appendaged sepals. There are two unappendaged sepals with hairy and glandular edges.

*Receptacle.*—Color: Green Group 143B. Shape: Funnel. Size: Small. Surface: Smooth.

*Peduncle.*—Length: Short (1½ to 2"). Surface: Smooth with some very fine hairs and an occasional gland. Color: Light Green. Strength: Stiff, erect, slender.

Bloom:

*Size.*—Medium. Average open size is 4".

*Borne.*—Singly and several together.

*Stems.*—Medium, strong (12 to 14").

*Form.*—When first open: High center. Permanence: Retains its form to the end, outer petals curl back, quill fashion.

*Petalage.*—Number of petals under normal condition: 30 to 35.

*Color.*—The upper side of the petals is Yellow Group 12B. The reverse side of the petals is Yellow Group 12B. The base of petals is Yellow. The major color on the upper side is Yellow Group 12B.

*Variegations.*—None.

*Discoloration.*—No change in the general tonality at the end of the first day. Generally no change at the end of the third day. However, if blooms are exposed to extremely bright hot sun, there will be some fading in the outer petals.

*Fragrance.*—Slight.

Petals:

*Texture.*—Medium.

*Shape.*—Deltoid.

*Form.*—Tips slightly recurved, edges slightly quilled.

*Arrangement.*—Imbricated. Petaloids in the center: Very few.

*Persistence.*—Drop off cleanly.

*Lastingness.*—On the plant: Fair (3 to 5 days). As a cut flower: Fair (about 5 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Reddish.

*Stigmas.*—Color: Greenish white.

Form: Bush.

Growth: Vigorous, upright, branching.

Foliage: Number of leaflets on normal mid-stem leaves: 5.

*Size.*—Medium (4" wide × 6" long).

*Quantity.*—Abundant.

*Color.*—New foliage: Reddish-bronze. Old foliage: Matte green.

Leaflets:

*Shape.*—Pointed oval.

*Texture.*—Upper side: Smooth.

*Edge.*—Serrated.

*Serration.*—Single.

*Petiole rachis.*—Color: Green.

*Petiole underside.*—Rough with prickles and glands.

*Stipules.*—Long to medium (½ to ¾"), bearded.

*Disease resistance.*—Susceptible to mildew but highly resistant to rust. Some tolerance for blackspot. More resistant than Sunbright, less resistant than Sunflare under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (¼ to 7/16"), hooked downward.

*Color when young.*—Red.

Small Prickles:

*Quantity.*—On main stalks: Few. On laterals: Few.

*Color.*—Green.

I claim:

1. A new and distinct variety of rose plant of the Grandiflora class, substantially as herein shown and described, characterized particularly as to novelty by the unique combination of its vigorous, upright growth habit, bright, non-fading yellow flowers, resistance to rust, tolerance to blackspot, and high production of flowers suitable for cutting from the garden.

* * * * *

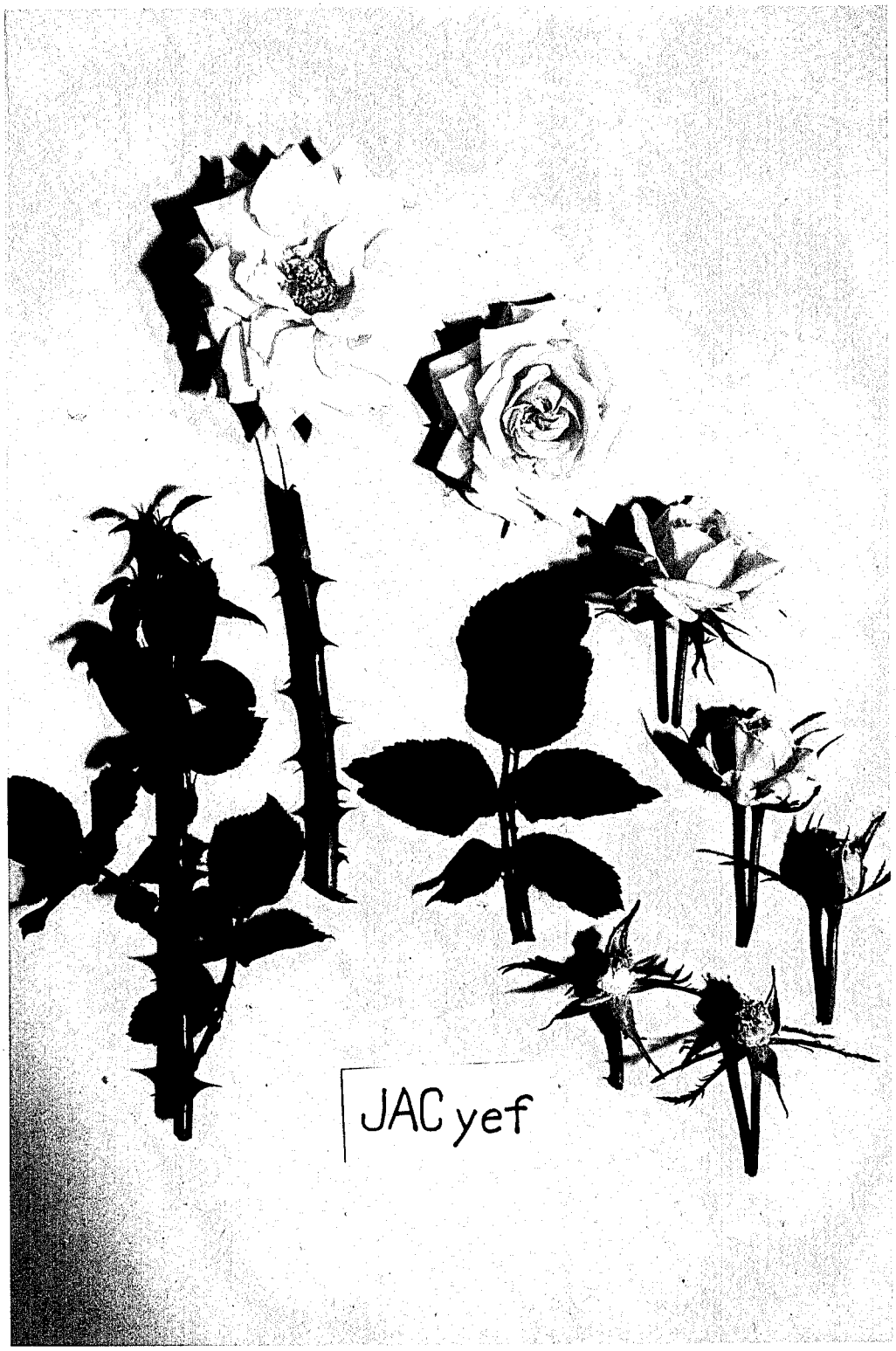
JAC yef